(12) United States Patent
Libera et al.

(10) Patent No.: US 7,887,843 B2
(45) Date of Patent: Feb. 15, 2011

(54) METHOD FOR IN VITRO PRODUCTION OF THREE-DIMENSIONAL VITAL CARTILAGE TISSUE AND USE THEREOF AS TRANSPLANT MATERIAL

(75) Inventors: Jeanette Libera, Berlin (DE); Ursula Anderer, Berlin (DE); Karl-Gerd Fritsch, Berlin (DE); Olivera Josimovic-Alasevic, Berlin (DE)

(73) Assignee: Co.don Aktiengesllschaft, Teltow (DE)

( * ) Notice: Subject to any disclaimer, the term of this patent is extended or adjusted under 35 U.S.C. 154(b) by 887 days.

(21) Appl. No.: 10/239,701

(22) PCT Filed: Mar. 9, 2001

(86) PCT No.: PCT/EP01/02698

§ 371 (c)(1),
(2), (4) Date: Jan. 21, 2003

(87) PCT Pub. No.: WO01/68811

PCT Pub. Date: Sep. 20, 2001

(65) Prior Publication Data

US 2003/0153078 A1  Aug. 14, 2003

(30) Foreign Application Priority Data

Mar. 13, 2000  (DE) ............................... 100 13 223

(51) Int. Cl.
*A61K 9/14* (2006.01)
(52) U.S. Cl. .................... 424/489; 424/93.7; 435/1.1; 435/383; 623/23.72; 623/23.73
(58) Field of Classification Search ............. 424/93.7; 435/372, 383
See application file for complete search history.

(56) References Cited

U.S. PATENT DOCUMENTS

| | | | | |
|---|---|---|---|---|
| 5,655,546 A | * | 8/1997 | Halpern | 128/898 |
| 5,723,331 A | * | 3/1998 | Tubo et al. | 435/366 |
| 6,152,964 A | * | 11/2000 | Van Blitterswijk et al. | 623/23.72 |
| 6,299,650 B1 | * | 10/2001 | Van Blitterswijk et al. | 623/23.63 |
| 6,811,776 B2 | * | 11/2004 | Kale et al. | 424/93.7 |

OTHER PUBLICATIONS

Kato et al, PNAS, 1988, vol. 85, pp. 9552-9556.*
Mackay et al, Tissue Engineering, 1998, vol. 4, No. 4, pp. 415-428.*
Tosh et al, Biochemical Society Transactions, 2002, vol. 30, Part 2, pp. 51-55.*
Costar et al, British Journal of Ophthalmology, 1980, vol. 64, pp. 135-136.*
Vunjak-Novakovic et al, "Effects of Mixing on the Composition and Morphology of Tissue-Engineered Cartilage" (1996), AIChE Journal, vol. 42, No. 3, pp. 850-860.*
Sutherland, RM "Cell and Environment Interactions in Tumor Microregions: The Multicell Spheroid Model" (1988) Science, vol. 240, Issue 4849, p. 177-184.*

* cited by examiner

*Primary Examiner*—Allison M Ford
(74) *Attorney, Agent, or Firm*—Norris McLaughlin & Marcus, PA

(57) ABSTRACT

The invention relates to a remarkably simple method for the in vitro production of three-dimensional, vital and mechanically stable cartilage or bone tissue and to the use thereof as a transplantation material for treating cartilage or bone defects and degenerative diseases such as rheumatism or arthrosis, and to the use thereof in testing active substances and physical factors. The invention is also directed to the cartilage or bone tissue and therapeutical formulations produced thereby, e.g. injection solutions comprising such tissue.

17 Claims, 2 Drawing Sheets

METHOD FOR IN VITRO PRODUCTION OF THREE-DIMENSIONAL VITAL CARTILAGE TISSUE AND USE THEREOF AS TRANSPLANT MATERIAL

BACKGROUND OF THE INVENTION

The invention relates to a remarkably simple method for the in vitro production of three-dimensional, vital and mechanically stable cartilage or bone tissue and to the use thereof as a transplantation material for treating cartilage or bone defects and degenerative diseases such as rheumatism or arthrosis, and to the use thereof in testing active substances and physical factors. The invention is also directed to the cartilage or bone tissue and therapeutical formulations produced thereby, e.g. injection solutions comprising such tissue. According to the invention, most various cartilage and bone tissues can be produced, e.g. hyaline, elastic, fibrous, or connective tissue cartilages such as joint cartilage, nose cartilage, meniscus cartilage, or intervertebral cartilage.

In the field of tissue engineering, solutions to build up endogenous tissue have been sought for quite some time. To this end, endogenous cells with and without support material have been used on the one hand, and, on the other hand, support materials exclusively have been incorporated in the defect where, depending on the indication, it is possible to use absorbable or non-absorbable materials.

The use of support materials is disadvantageous in that decomposition products thereof may affect other tissues, and when using non-autogenous support materials, i.e., those not derived from the patient, immune reactions or infections with animal or human pathogens may arise.

One familiar method using endogenous cells is transplantation of cartilage and bone cells, which is used in the treatment of cartilage and bone defects. In this method, the potential of cartilage and bone cells is utilized to build up new tissue in vivo. Thus, for example, cartilage or bone biopsies are taken from a patient, cartilage or bone cells are isolated therefrom, grown by means of cell culturing, and the cells are subsequently transplanted into the patient in the region of the tissue defect, e.g. by injecting. There, the cells form new tissue, thus effecting complete repletion of the defect.

The above-mentioned methods achieve build up of tissue in the body subsequent to applying the cell transplant or incorporating the support materials.

However, tissue engineering is also directed to the in vitro prefabrication of endogenous tissue. A variety of methods are known from the literature (cf., DE 195 40 487, WO 97/46665, DE 197 52 900, U.S. Pat. No. 5,932,459), which methods require special apparatus or supports, involve numerous process steps, or necessitate addition of growth-stimulating compounds representing foreign substances to the body. It was therefore the object of the present invention to provide a preferably simple method of producing typical cartilage or bone tissue, which method allows for the production of vital, three-dimensional and mechanically stable tissue which is suitable for transplantation and ensures rapid adhesion in the body and rapid repletion of the cartilage or bone defect. Furthermore, the tissue produced in vitro should not trigger any immunological reaction in the organism receiving the transplant.

SUMMARY OF THE INVENTION

Surprisingly, it has been found that the above object can be accomplished by using the simple method specified in claim 18.

BRIEF DESCRIPTION OF THE DRAWINGS

The invention will now be described in greater detail with reference to the drawings, wherein:

According to the invention, patient-derived tissue biopsies or samples or mesenchymal stem cells, e.g. from peripheral blood or bone marrow are used as starting material. The tissue-building cells are isolated from the biopsies according to conventional methods, using enzymatic digestion of the tissue, migration, or reagents recognizing the target cells. According to the invention, these cells are then subjected to stationary culturing in suspension in a simple fashion, using conventional culture medium in cell culture vessels with hydrophobic surface and tapering bottom, until a three-dimensional cell aggregate is formed which includes at least 40% by volume, preferably at least 60% by volume and up to a maximum of 95% by volume of extracellular matrix (ECM) having differentiated cells embedded therein. The cell aggregate having formed has an outer region wherein cells capable of proliferation and migration are present. The structure of the cell aggregates obtained according to the invention is illustrated by the microscopic photographs in FIGS. 1 and 1a; FIG. 1 shows a detail enlargement of the cross-section of a cell aggregate according to the invention, with vP as the zone where initial tissue-specific matrix proteins occur, and M as the zone where tissue-specific matrix proteins are formed; FIG. 1a illustrates the entire cell aggregate including the outer zone of proliferative and migratory cells P (zone of protein S 100 expression).

It is noteworthy that all the cells integrated in the spheroids produced according to the invention survive, and that the cells inside do not necrotize even after an advanced period of culturing. With increasing time of cultivation, the cells inside the aggregates undergo differentiation to form spheroids consisting of ECM, differentiated cells and a peripheral proliferation zone. The process of formation of the tissue-specific matrix with embedded cells is highly similar to the process of tissue formation or neogenesis and reorganization in the body. During differentiation in cell culture, the spacing of the aggregated cells increases due to formation of the tissue-specific matrix. A tissue histology develops inside the spheroids which is highly similar to natural tissue. As in natural cartilage, the cells inside the spheroids are supplied with nutrients by way of diffusion only. During the further course of spheroid production, a zone of cells capable of proliferation and migration is formed at the boundary of the spheroids. This zone is invaluably advantageous in that following incorporation of the spheroids in defects, the cells situated in this peripheral zone are capable of migrating to make active contact with the surrounding tissue and/or enable integration of the tissue produced in vitro in the environment thereof. Thus, the tissue-specific cell aggregates produced are excellently suitable for use in the treatment of tissue defects and in the in vitro and in vivo neogenesis of tissue.

Depending on the size of the tissue defect to be treated, it can be advantageous to transplant larger pieces of tissue at an early stage so as to achieve more rapid repletion of the defect.

In this event, at least two or preferably more of the cell aggregates obtained are fused by continuing culturing thereof under the same conditions and in the same culture vessels as described above until the desired size is reached.

Figure 1:
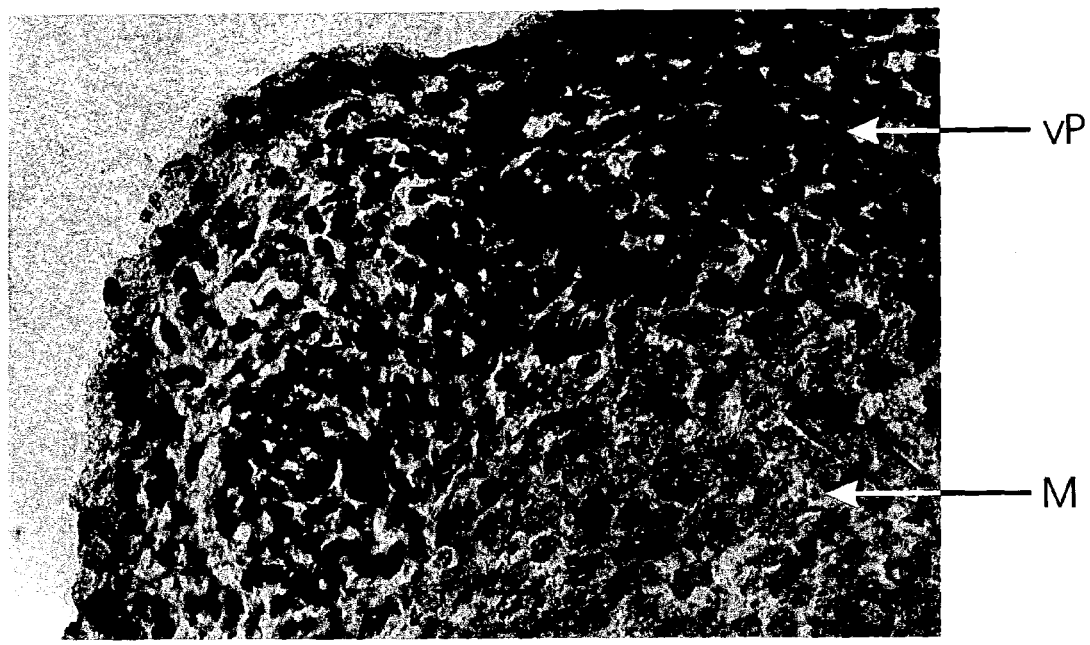
FIG. 1 illustrates a cross-sectional view of a cell aggregate in an embodiment of the present invention.
Figure 1A:
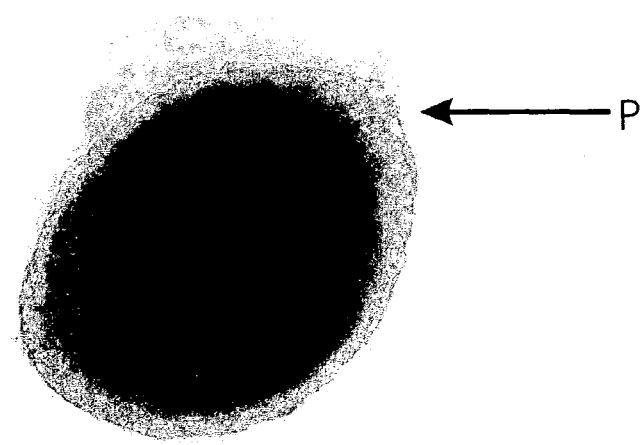
FIG. 1a illustrates a cell aggregate in an embodiment of the present invention.
Figure 1B:
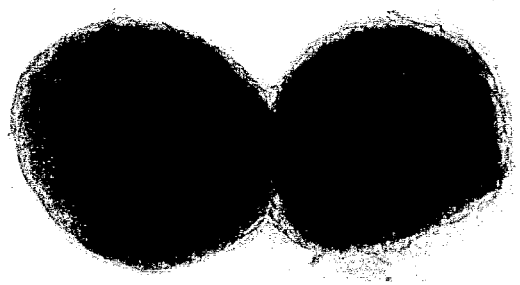
FIG. 1b illustrates two fusing spheroids in an embodiment of the present invention.

FIG. 1b shows two fusing spheroids after one day.

Figure 1C:
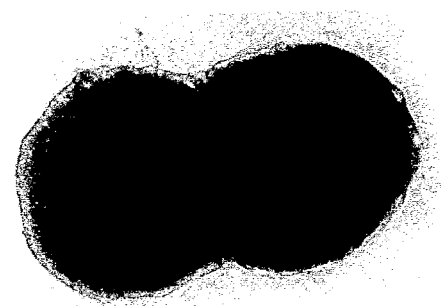
FIG. 1c illustrates two fusing spheroids in an embodiment of the present invention.
Figure 1D:
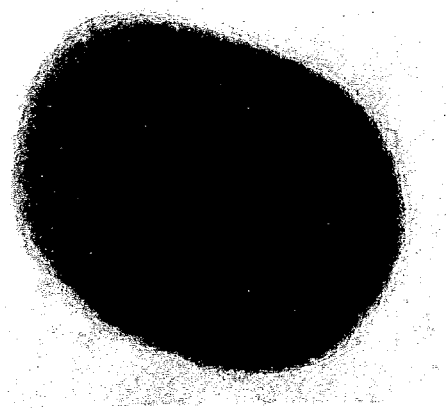
FIG. 1d illustrates spheroids that are completely fused in an embodiment of the present invention.

FIG. 1c shows that only some hours later, the boundary between the two spheroids cannot be recognized any longer. After another week the spheroids are completely fused, and a larger in vitro tissue patch has formed (FIG. 1d). The structure of the larger cell aggregates thus obtained is identical to that of the spheroids obtained initially. They may include ECM up to a maximum of 95%, and all of the cells included in the piece of tissue obtained exhibit vitality.

The cartilage or bone tissue obtained is extraordinarily stable. The cell aggregates can be compressed to ¾ of their diameter without breaking or decomposing e.g. when injected into the body by means of a needle. The pieces of tissue can be taken out of the cell culture vessel using pincers or a pipette.

In an advantageous embodiment of the invention, the cells obtained from the patient are first grown in a monolayer culture in a per se known fashion to have sufficient cartilage or bone cells available for suspension culturing according to the invention. Passage of the cells in monolayer culture is kept as low as possible. After reaching the confluent stage, the cells grown in monolayer are harvested and cultured according to the inventive method in suspension as described above.

A medium usual both for suspension and monolayer culture, e.g. Dulbecco's MEM, with addition of serum, can be used as cell culture medium. It is preferred to use DMEM and HAMS at a ratio of 1:1. However, to avoid an immunological response of the patient to the tissue produced in vitro, it is preferred to use autogenous serum from the patient as serum. It is also possible to use xenogeneic or allogenic serum.

According to the invention, no antibiotic, fungistatic agents or other auxiliary substances are added to the culture medium. It has been found that only autogenous, xenogeneic or allogenic cultivation of the cells and cell aggregates and cultivation with no antibiotic and fungistatic agents allow for non-affected morphology and differentiation of the cells in the monolayer culture and undisturbed formation of the specific matrix within the cell aggregates. Furthermore, by avoiding any additive during the production, any immunological reaction is excluded when incorporating the tissue produced in vitro in a human or animal organism.

Quite surprisingly, indeed, growth factors or other growth-stimulating additives are required neither in suspension culturing, nor in monolayer culturing. Despite the absence of such additives, three-dimensional cell aggregates with tissue-specific properties are obtained after only two days of suspension culturing according to the invention. Obviously, the size depends on the number of introduced cells per volume of culture medium. For example, when incorporating $1 \times 10^7$ cells in 300 μl of culture medium, three-dimensional spheroids about 500-700 μm in diameter are formed within one week. For a tissue defect of 1 cm², it would be necessary to transplant about 100 of such spheroids, e.g. by injection. Another way would be in vitro fusion of small cell aggregates to form larger ones—as described above—and incorporation of the latter in the defect. According to the invention, it is preferred to use between $1 \times 10^4$ and $1 \times 10^7$ cells in 300 μl of culture medium to produce the small cell aggregates, more preferably $1 \times 10^5$ cells. Depending on the cell type and patient-specific characteristics, the spheroids having formed after several days are then cultured in a suitable culture medium for at least 2-4 weeks to induce formation of the tissue-specific matrix. From about one week of culturing on, it is possible to fuse individual spheroids in special cases, so as to increase the size of the tissue patch.

As cell culture vessels, the inventive cultivation in suspension requires the use of those having a hydrophobic, i.e., adhesion-preventing surface, such as polystyrene or Teflon. Cell culture vessels with a non-hydrophobic surface can be hydrophobized by coating with agar or agarose. Further additives are not required. Preferably, well plates are used as cell culture vessels. For example, 96-well plates can be used to produce small cell aggregates, and 24-well plates to produce said fused aggregates.

According to the invention, the cell culture vessels must have a tapering, preferably concave bottom. It has been found that the tissue of the invention will not be formed in flat-bottomed vessels. Apparently, the depression is useful in finding the cells.

The invention is also directed to the cartilage or bone tissue produced according to the above-described method, which tissue can be used as an autogenous, xenogeneic or allogenic transplantation material for treating cartilage or bone defects and degenerative diseases such as arthrosis or rheumatism. To this end, the cell aggregates of the invention produced in vitro are injected into the diseased or degraded tissue. To do so, an injection needle or other suitable application system must have at least the diameter of the spheroids. The cells within the zone of proliferative and migratory cells at the boundary of the spheroids rapidly grow into the surrounding tissue, enabling rapid integration of the tissue produced in vitro, and represent a potential for neogenesis of tissue in the region near the spheroids, because these cells still exhibit proliferation and formation of matrix. Representing an advancement compared to previous methods, this treatment can be effected by means of arthroscopy.

The invention therefore is also directed to therapeutic formulations comprising the cartilage or bone tissue according to the invention, e.g. injection solutions. The invention is also directed to the use of the cartilage or bone tissue of the invention in testing various factors, e.g. active substances and physical factors having an effect on the formation and differentiation of matrix and cells, for example; physical factors can be e.g. pressure or electric fields. To this end, cell spheroids are produced according to the invention, the medications to be tested are added at various stages of maturity, and most various parameters of spheroid formation and maturing are characterized. Compared to conventional drug testing using animals or tumor systems, these tests are highly patient-specific and enable individual diagnosis as a result of using autologous material only.

Without intending to be limiting, the invention will be illustrated in more detail below with reference to the examples.

EXAMPLES

Example 1

In Vitro Production of Cartilage Tissue

A biopsy is taken from a patient from a region of hyaline, healthy cartilage. Chondrocytes are isolated from this biopsy, using enzymatic digestion by incubation with collagenase solution. Following separation of the isolated cells from the undigested cartilage tissue, the cells are transferred in cell culture flasks and, following addition of DMEM/HAMS F12 culture medium (1/1) and 10% autologous serum from the patient, incubated at 37° C. and 5% $CO_2$. The medium is exchanged twice a week. After reaching the confluent stage, the cell layer is washed with physiological saline solution and harvested from the cell culture surface using trypsin. Following another washing, $1\times10^5$ cells each time are transferred in a cell culture vessel coated with agarose. After one day, the first cells arrange into aggregates. These aggregates are supplied with fresh medium every second day and cultured for at least 2 weeks.

After only one week, type II collagen and proteoglycans were detected in the aggregates. To this end, a specific antibody to type II collagen was used. The primary antibody bound to type II collagen was detected using a second antibody and an ABC system coupled thereto. That is, the second antibody has coupled the enzyme alkaline phosphatase via avidin-biotin thereto, which enzyme effects reaction of the substrate fuchsin to form a red dye.

The proteoglycans were detected by means of Goldner staining. Type II collagen and proteoglycans are components of the cartilage matrix in vivo, representing the most important structural proteins which are of crucial significance for cartilage function.

At the same time, the protein S 100 specific for cartilage cells was detected in the outer layer of the aggregates. S 100 is neither expressed in bone tissue nor in connective tissue. It is only these latter tissues which also could have formed. Consequently, the tissue having developed was unambiguously proven to be cartilage tissue.

After culturing for 1-2 weeks, the cells are still close together. With increasing cultivation time, the proportion of extracellular matrix increases and the proportion of cells decreases. After one week, at least 40% ECM can be detected, and after 3 weeks, about 60% ECM has already developed. After 3 months of cartilage tissue cultivation, the proportion of ECM has increased to 80-90%. That is, cartilage-like tissue has been built up inside the aggregates produced, which tissue in its structure corresponds to in vivo cartilage and is also capable of assuming the function of cartilage tissue.

Example 2

Transplantation of Cartilage Tissue

The tissue produced in Example 1 (about 200 spheroids, each one comprised of $1\times10^5$ cells) was taken up in physiological saline solution and injected into a cartilage defect in the subject about 1 cm² in size and covered with periosteum. Repletion of the cartilage defect with cartilage tissue was determined already within 1 to 2 months, while repletion of a defect of such a size can be detected not before 6-12 months when using the previous transplantation of juvenile cartilage cells merely grown in vitro. Thus, in addition to assuming the mechanical function of the tissue produced, the cartilage tissue of the invention produced in vitro ensures rapid integration of the produced tissue patches by virtue of the proliferative and migratory cells in the outer layer of the aggregates. Consequently, structure and function of the tissue patches also allow for rapid repair of defects and degenerate cartilage tissue.

Example 3

In Vitro Production of Bone Tissue

A bone biopsy is taken from a patient from a spongiosa region. Osteoblasts are isolated from this biopsy, using enzymatic digestion by incubation with collagenase solution. Following separation of the isolated cells from the undigested bone tissue, the cells are transferred in cell culture flasks and, following addition of DMEM/HAMS F12 culture medium (1/1) and 10% autologous serum from the patient, incubated at 37° C. and 5% $CO_2$. The medium is exchanged twice a week. After reaching the confluent stage, the cell layer is washed with physiological saline solution and harvested from the cell culture surface using trypsin. Following another washing, $1\times10^5$ cells each time are transferred in a cell culture vessel coated with agarose. After one day, the first cells arrange into aggregates. These aggregates are supplied with fresh medium every second day and cultured for at least 2 weeks.

After only one week, type I collagen and proteoglycans were detected in the aggregates. To this end, a specific antibody to type I collagen was used. By detecting collagen I, unambiguous proof is provided that this is not cartilage tissue. The primary antibody bound to type I collagen was detected using a second antibody and an ABC system coupled thereto. That is, the second antibody has coupled the enzyme alkaline phosphatase via avidin-biotin thereto, which enzyme effects reaction of the substrate fuchsin to form a red dye.

As in Example 1, the proteoglycans were detected by means of Goldner staining. Type I collagen and proteoglycans are components of the bone matrix in vivo, representing the most important structural proteins which are of crucial significance for bone function.

At the same time, proliferative bone cells were detected in the outer layer of the aggregates.

After culturing for 2 weeks, the cells are still close together. With increasing cultivation time, the proportion of extracellular matrix increases and the proportion of cells decreases. After one week, at least 40% ECM can be detected, and after 3 weeks, about 60% ECM has already developed. That is, bone-like tissue has been built up inside the aggregates produced, which tissue in its structure corresponds to in vivo bone and is also capable of assuming the function of bone tissue.

Example 4

Transplantation of Bone Tissue

The tissues produced in Example 3 (about 50 patches) were taken up in physiological saline solution and injected in the region of a reluctantly healing bone fracture. It has been determined that it is possible to induce the process of bone healing whereas healing of the fracture had taken place only after several months if the defect had remained untreated. Accordingly, the bone tissue cultured in vitro ensures rapid integration of the tissue into the surrounding tissue and repletion of bone defects. Consequently, structure and function of the tissue patches permit healing of bone defects, induction of osteosynthesis, and treatment of degenerative bone diseases.

The invention claimed is:

1. A method for treating a defect in cartilage tissue of a patient, the method consisting of:
   (a) isolating cartilage cells from a human or animal organism,
   (b) subjecting said cells to stationary suspension culture in a cell culture vessel having a hydrophobic surface and tapered bottom to form a cell aggregate in the form of a spheroid,
   wherein said culturing is performed in a cell culture medium consisting of:
      (i) DMEM, or DMEM and HAMS, and
      (ii) a serum chosen as one of autogenous, xenogeneic and allogenic with respect to the patient, and wherein said spheroid comprises at least 40% by volume of extracellular matrix (ECM), differentiated cells embedded within the ECM, has an outer region comprising cells capable of proliferation and migration, and has a size defined as one of:
(i) a diameter of 500-700 μm,
(ii) containing $1\times10^4$ to $1\times10^7$ cells, or
(iii) a size that may be produced in a well of a 96-well cell culture plate,
(c) repeating steps (a) and (b) to obtain a plurality of spheroids as a transplant material, or, alternatively,
(c') repeating steps (a) and (b) to form at least two spheroids, and then fusing the at least two spheroids by culturing the at least two spheroids together according to (b) to obtain a single spheroid as a transplant material, and
(d) transplanting the transplant material into the defect of the patient,
wherein between (a) and (b) the cells may optionally be grown in a monolayer culture, or in a case in which the cell culture vessel has a non-hydrophobic surface, between (a) and (b) the surface of the cell culture vessel can be rendered hydrophobic by coating the surface with agar or agarose.

2. The method according to claim 1, wherein the culture vessels are well plates.

3. The method according to claim 1, wherein the tapered bottom is a concave bottom.

4. The method according to claim 1, wherein the spheroid comprises at least 60% by volume of ECM.

5. The method according to claim 1, wherein the serum of the cell culture medium is autogenous with respect to the patient.

6. The method according to claim 1, wherein the cell culture medium consists of (i) DMEM and HAMS, and (ii) serum.

7. The method according to claim 6, wherein the serum is autogenous with respect to the patient.

8. The method according to claim 1, wherein the cell culture medium consists of (i) DMEM and HAMS at a ratio of 1:1, and (ii) serum.

9. The method according to claim 8, wherein the serum is autogenous with respect to the patient.

10. The method according to claim 1, wherein the transplant material transplanted in step (d) comprises up to 200 spheroids/cm$^2$ defect.

11. The method according to claim 1, wherein said (d) transplanting is performed arthroscopically.

12. A method for making cartilage tissue transplant material to treat a defect in cartilage tissue of a patient, the method consisting of:
(a) subjecting cartilage cells isolated from a human or animal organism to stationary suspension culture in a cell culture vessel having a hydrophobic surface and tapered bottom to form a cell aggregate in the form of a spheroid,
wherein said culturing is performed in a cell culture medium consisting of:
(i) DMEM, or DMEM and HAMS, and
(ii) a serum chosen as one of autogenous, xenogeneic and allogenic with respect to the patient, and
wherein said spheroid comprises at least 40% by volume of extracellular matrix (ECM), differentiated cells embedded within the ECM, has an outer region comprising cells capable of proliferation and migration, and has a size defined as one of:
(i) a diameter of 500-700 μm,
(ii) containing $1\times10^4$ to $1\times10^7$ cells, or
(iii) a size that may be produced in a well of a 96-well cell culture plate, and
(b) repeating step (a) to obtain a plurality of spheroids as the cartilage tissue transplant material, or, alternatively,
(b') repeating step (a) to form at least two spheroids, and then fusing the at least two spheroids by culturing the at least two spheroids together according to step (a) to obtain a single spheroid as the cartilage tissue transplant material,
wherein the cartilage tissue transplant material is produced in vitro and is three-dimensional vital cartilage tissue of a different size or shape than a defect of a patient.

13. The method according to claim 12, wherein the serum is autogenous with respect to the patient.

14. A method of treating a cartilage defect in a patient, comprising transplanting into said defect a transplant material comprising a plurality of cartilaginous spheroids,
wherein each of said spheroids comprises at least 40% by volume of extracellular matrix (ECM), differentiated cells embedded within the ECM, has an outer region comprising cells capable of proliferation and migration, and has a size defined as one of:
(i) a diameter of 500-700 μm,
(ii) containing $1\times10^4$ to $1\times10^7$ cells, or
(iii) a size that may be produced in a well of a 96-well cell culture plate,
wherein the transplant material is one of autogenous, xenogeneic or allogeneic with respect to the patient, and
wherein the transplant material comprises a number of spheroids which is insufficient to initially fill the defect, but which will grow to sufficiently fill the defect over time, irrespective of the shape or size of the defect.

15. The method according to claim 14, wherein the defect is a result of arthrosis or rheumatism.

16. The method according to claim 14, wherein up to 200 spheroids/cm$^2$ defect are transplanted.

17. The method according to claim 14, wherein said transplanting is performed arthroscopically.

* * * * *